(12) United States Patent
Griesbach, III et al.

(10) Patent No.: US 9,327,042 B2
(45) Date of Patent: May 3, 2016

(54) MULTI-PANEL STERILIZATION ASSEMBLY WITH STRETCH COMPONENTS

(71) Applicant: AVENT, INC., Alpharetta, GA (US)

(72) Inventors: Henry L. Griesbach, III, Clarkston, GA (US); Azeema P. Ameerally, Alpharetta, GA (US); Michael F. Kalmon, Ball Ground, GA (US)

(73) Assignee: Avent, Inc., Alpharetta, GA (US)

( * ) Notice: Subject to any disclaimer, the term of this patent is extended or adjusted under 35 U.S.C. 154(b) by 35 days.

(21) Appl. No.: 14/307,875

(22) Filed: Jun. 18, 2014

(65) Prior Publication Data

US 2015/0367012 A1    Dec. 24, 2015

(51) Int. Cl.
| | |
|---|---|
| *B65D 65/22* | (2006.01) |
| *A61L 2/28* | (2006.01) |
| *B65D 65/06* | (2006.01) |
| *B65D 65/08* | (2006.01) |
| *B65D 65/24* | (2006.01) |
| *A61L 2/26* | (2006.01) |
| *A61B 19/02* | (2006.01) |

(52) U.S. Cl.
CPC ... *A61L 2/28* (2013.01); *A61L 2/26* (2013.01); *B65D 65/06* (2013.01); *B65D 65/08* (2013.01); *B65D 65/24* (2013.01); *A61B 2019/0201* (2013.01); *A61L 2202/181* (2013.01)

(58) Field of Classification Search
CPC .... B65D 65/22; A61L 2/26; A61L 2202/181; Y10T 428/24008
USPC .............................. 229/87.01, 87.03; 422/294
See application file for complete search history.

(56) References Cited

U.S. PATENT DOCUMENTS

| | | |
|---|---|---|
| 3,680,772 A | 8/1972 | Hoover |
| 3,746,152 A | 7/1973 | Allen |
| 4,041,203 A | 8/1977 | Brock et al. |
| 4,342,392 A * | 8/1982 | Cox ............ A61B 19/08 128/855 |
| 4,652,487 A | 3/1987 | Morman |
| 4,655,760 A | 4/1987 | Morman et al. |
| 4,657,802 A | 4/1987 | Morman |
| 4,720,415 A | 1/1988 | Vander Wielen et al. |
| 4,781,966 A | 11/1988 | Taylor |
| 4,789,699 A | 12/1988 | Kieffer et al. |
| 4,801,480 A | 1/1989 | Panza et al. |
| 4,965,122 A | 10/1990 | Morman |
| 4,981,747 A | 1/1991 | Morman |
| 5,035,687 A | 7/1991 | Sandbank |
| 5,143,679 A | 9/1992 | Weber et al. |
| 5,151,092 A | 9/1992 | Buell et al. |

(Continued)

FOREIGN PATENT DOCUMENTS

| | | |
|---|---|---|
| WO | WO 2011/016006 A2 | 2/2011 |
| WO | WO 2013/046186 | 4/2013 |
| WO | WO 2013/046187 A2 | 4/2013 |

OTHER PUBLICATIONS

Search Report and Written Opinion for PCT/US2015/035973 dated Sep. 21, 2015, 10 pages.

*Primary Examiner* — Jes F Pascua
(74) *Attorney, Agent, or Firm* — Dority & Manning, P.A.

(57) ABSTRACT

The multi-panel sterilization assembly includes a barrier panel formed of permeable material having barrier properties, side wings that can include grip portions for folding or unfolding the barrier panel; and a fold protection panel. The fold protection panel and/or either or both wings may be made from a stretchable material.

18 Claims, 2 Drawing Sheets

(56) References Cited

U.S. PATENT DOCUMENTS

| | | |
|---|---|---|
| 5,167,897 A | 12/1992 | Weber et al. |
| 5,196,000 A | 3/1993 | Clear et al. |
| 5,226,992 A | 7/1993 | Morman |
| 5,336,545 A | 8/1994 | Morman |
| 5,514,470 A | 5/1996 | Haffner et al. |
| 5,635,134 A | 6/1997 | Bourne et al. |
| 6,006,985 A | 12/1999 | Hawkins |
| 6,276,032 B1 * | 8/2001 | Nortman ............ A44B 18/0065 24/572.1 |
| 6,391,260 B1 | 5/2002 | Davis et al. |
| 6,406,764 B2 | 6/2002 | Bayer |
| 6,578,348 B1 | 6/2003 | Banks |
| 7,560,082 B2 | 7/2009 | Stecklein et al. |
| 7,968,479 B2 * | 6/2011 | Welch ............... A61F 13/15593 156/229 |
| 8,261,963 B2 | 9/2012 | Gaynor et al. |
| 2001/0036519 A1 | 11/2001 | Bayer |
| 2003/0045856 A1 | 3/2003 | Couture et al. |
| 2004/0178104 A1 * | 9/2004 | Mizutani ........... A61F 13/15211 206/440 |
| 2005/0163654 A1 | 7/2005 | Stecklein et al. |
| 2009/0134049 A1 * | 5/2009 | Melik ................. A61F 13/4902 206/370 |
| 2009/0280028 A1 * | 11/2009 | Muggli ..................... A61L 2/10 422/24 |
| 2011/0033137 A1 * | 2/2011 | Gaynor ................ A61B 19/026 383/105 |
| 2012/0079795 A1 * | 4/2012 | Smith .................... A61B 19/02 53/461 |
| 2012/0202000 A1 * | 8/2012 | Bricker ..................... A61L 2/26 428/99 |
| 2013/0001283 A1 * | 1/2013 | Friderich .............. B65D 65/06 229/87.01 |
| 2013/0020380 A1 * | 1/2013 | Gaynor ................ A61B 19/026 229/87.01 |
| 2013/0081355 A1 | 4/2013 | Gaynor et al. |
| 2013/0092724 A1 * | 4/2013 | Gaynor ..................... A61L 2/26 229/87.05 |
| 2015/0083627 A1 * | 3/2015 | Gorman ............... B65D 75/004 206/439 |

\* cited by examiner

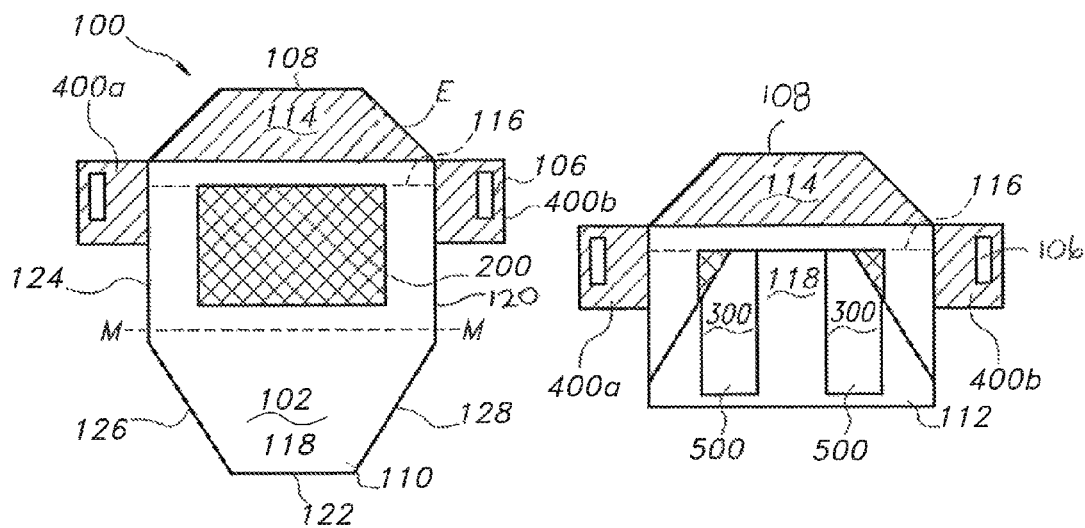
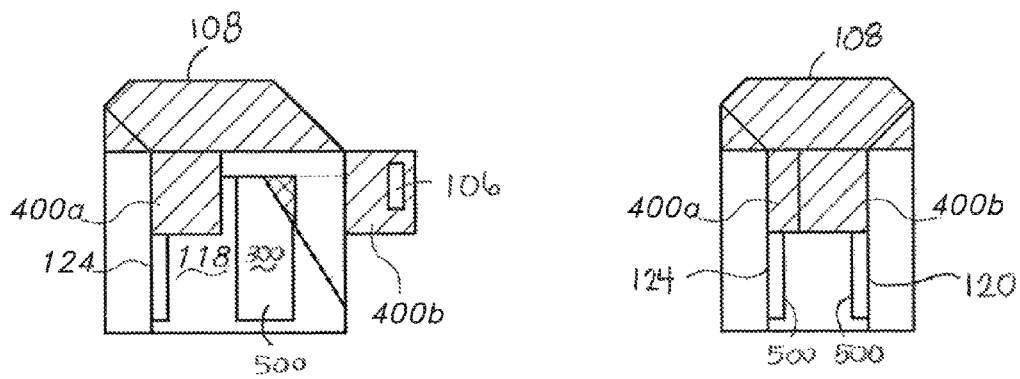
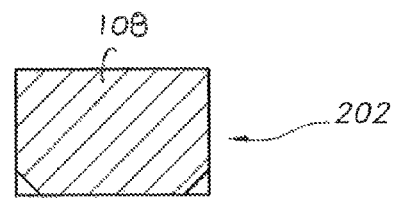
FIG. 1A  FIG. 1B
FIG. 1C  FIG. 1D
FIG. 1E

MULTI-PANEL STERILIZATION ASSEMBLY WITH STRETCH COMPONENTS

The present disclosure relates in general to disposable wraps used to contain content to be sterilized and store that content aseptically until use.

Conventional disposable sterilization wrap is a flat, featureless sheet of material that may occasionally contain one or more additional layers of material for strength or absorbency. For example, U.S. Pat. No. 5,635,134 to Bourne, et al. discloses a multi-ply sterilization wrap which is formed by joining one or more sheets of sterilization wrap (e.g., two separate sheets or one sheet folded over) together to form two similarly sized, superposed panels that allow convenient dual wrapping of an article. As another example, U.S. patent application publication 2001/0036519 by Robert T. Bayer discloses a two ply sterilization wrap that is formed of a single sheet of sterilization wrap material which is folded to form two similarly sized, superposed panels that are bonded to each other. As yet another example, U.S. patent application publication 005/0163654 by Stecklein, et al. discloses a sterilization wrap material that has a first main panel and a second panel that is smaller than the main panel. The second panel is superposed and bonded to the central portion of the main panel such that it is contained entirely within the main panel to reinforce the main panel and/or provide additional absorbency.

US patent application publication 2013/0081355 to Gaynor et al. provides an assembly, package or system that reduces the amount of sterilization wrap material needed for the sterile processing of an instrument tray or article and eliminates the need to grasp the sterilization wrap material to unfold wrap. This assembly reduces the amount of sterilization fabric that can be used in an extended or enhanced steam or heat sterilization process, and that simplifies the task of unwrapping a sterilized instrument tray or article while reducing or avoiding the likelihood that the sterilization fabric will fold back onto itself during unwrapping. It has been found, however, that minor shifts in fold position can occur and can lead to loose folds and movement of the container within the wrap. This movement can lead to abrasion induced hole formation.

It would be useful to have a sterilization wrap that did not allow movement of the container within the wrap. It would also be useful to have a wrap that provided a visual cue that sterilant had penetrated the folded wrap.

SUMMARY OF THE DISCLOSURE

The problems described above are addressed by the present disclosure which encompasses a multi-panel sterilization assembly having stretch components. The stretch component may be, for example, the fold protection panel and/or either or both wings used to secure the multi-panel sterilization assembly. The stretch component allows the component to "correct" for less than optimal positioning of the fold protection panel against the barrier panel, allowing a greater range in placement of the panel attachment means. The stretch component holds the folds tighter around the container.

When the stretch component is made to shrink when exposed to sterilizing conditions, they desirably change dimensions sufficiently to provide an obvious visual signal about successful sterilant penetration. The stretch component further may include an agent that changes color upon exposure to sterilizing conditions, further aiding in the provision of a visual cue.

These and other features and advantages of the disclosure will become more apparent to one skilled in the art from the following description and claims when read in light of the accompanying drawings.

DESCRIPTION OF THE DRAWINGS

The present disclosure will be better understood by reading the Detailed Description of the Disclosure with reference to the accompanying drawing figures, in which like reference numerals denote similar structure and refer to like elements throughout, and in which:

FIGS. 1A through 1E are illustrations of an exemplary sequence of folding an exemplary disposable flexible multi-panel sterilization assembly including side wings and pull tabs having spaced apart pull locations, prior to sterilization.

FIG. 1A illustrates the completely unfolded assembly with the content (or item) to be sterilized.

FIG. 1B illustrates the folding upwardly of the bottom end of the assembly, substantially covering the item to be sterilized.

FIG. 1C illustrates the folding over of the left side of the assembly, onto the folded bottom end and the item to be sterilized.

FIG. 1D illustrates the folding over of the right side of the assembly, onto the folded bottom end and the item to be sterilized.

FIG. 1E illustrates the folding over of the top end of the assembly, onto the folded bottom end and sides as well as the content to be sterilized, to make a package.

FIG. 2A illustrates the package from FIG. 1E after sterilization.

FIG. 2B illustrates the unfolding of the top end of the assembly, revealing the folded bottom end and sides.

FIG. 2C illustrates the unfolding of the right side of the assembly, revealing part of the folded bottom end.

FIG. 2D illustrates the unfolding of the left side of the assembly, revealing the rest of the folded bottom end.

FIG. 2E illustrates the completely unfolded assembly and the item, after sterilization.

DETAILED DESCRIPTION

Figure 2A:
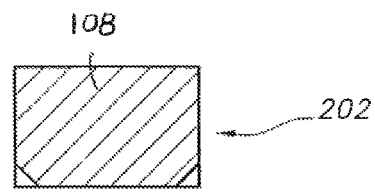
FIGS. 2A to 2E are illustrations of an exemplary sequence of unfolding an exemplary disposable flexible multi-panel sterilization assembly including side wings and pull tabs having spaced apart pull locations.

As used herein, the term "disposable" refers to a product that is so inexpensive that it may economically be discarded after only a single use. Products that are "disposable" are typically intended for single use. The term "single-use" refers to a product that is intended to be used for only once and is not intended to be re-used, re-conditioned, restored or repaired after that use. These products offer advantages in clinical settings by reducing the potential for contamination or infection. In addition, these products can enhance work flow since they are not collected and assembled for reprocessing and reuse.

As used herein, the term "multi-panel sterilization assembly" or "sterilization assembly" or "assembly" refers to a flexible article composed of fabric(s) and/or flexible material(s) that is wrapped around, folded around or otherwise encloses a non-sterile article or non-sterile content prior to sterilization. A sterilization assembly has multiple panels and/or sections providing specific physical properties, functional characteristics and/or structure that provide advantages for wrapping or folding, handling, strength, sterilization, storage after sterilization, and/or unwrapping or unfolding.

As used herein, the term "nonwoven" refers to a web or fabric that has a structure of individual fibers or filaments which are interlaid, but not in an identifiable repeating manner. Nonwovens have been, in the past, formed by a variety of processes known to those skilled in the art such as, for example, meltblowing, spunbonding and bonded carded web processes.

A typical sterilization tray with the dimensions of 10 inches (25.4 cm) by 20 inches (50.8 cm) by 5 inches tall (12.7 cm) typically requires a square piece of sterilization fabric having each side measuring 45 inches for wrapping and sterile processing. This large size piece is needed so that the corner of the fabric can be folded all the way across the top of the tray with some additional excess material so that the preparer of the tray feels confident that the contents are covered and that the piece of fabric will stay down and not spring back. Using a 45 inch, square piece of fabric means that 2025 square inches of material (approximately 13,064 square centimeters) is being used to enclose a tray with a surface area of just 700 square inches (approximately 4,516 square centimeters). In other words, this traditional method requires almost three square inches of material to cover every square inch of a tray of surgical instruments.

The multi-panel sterilization assembly includes a barrier panel formed of permeable material having barrier properties, side wings that can include grip portions for folding or unfolding the barrier panel; and a fold protection panel. The barrier panel has a first end and a second end opposite the first end, a first edge and a third edge, each such edge being generally perpendicular to the first end, and a midpoint to generally delineate the barrier panel into a content receiving region extending from approximately the first end to the midpoint and a content covering region extending from the midpoint to approximately the second end. The side wings are desirably located between the first end and the midpoint of the barrier panel and at or near the first edge and the third edge. The fold protection panel is in juxtaposed communication with the barrier panel such that after folding the content covering region and the first and third edges over the content receiving region, the fold protection panel covers them. The fold protection panel and/or either or both wings may be made from a stretchable material.

The flexible multi-panel sterilization assembly has a barrier panel made with a permeable sheet material having barrier properties, the barrier panel includes a first surface and a second opposing surface, a first end and a second end opposite the first end, a first edge and a third edge, each such edge being generally perpendicular to the first end. The second edge is generally opposite the first end. The barrier panel has a maximum width that is the distance from the first edge to the third edge and a maximum length that is the distance from the first end to the second end. The barrier panel has a midpoint along the length and extending between the first edge and the third edge to generally delineate the barrier panel into a content receiving region extending from approximately the first end to the midpoint and a content covering region extending from the midpoint to approximately the second end.

The assembly has side wings located between the first end and the midpoint of the barrier panel and at or near the first edge and the third edge. The side wings include grip portions for folding or unfolding the barrier panel. The assembly has a fold protection panel in juxtaposed communication with the barrier panel. The fold protection panel is made with a permeable sheet material and includes a proximal end generally adjacent the first end of the barrier panel, a distal end generally opposite the proximal end and at least a first edge and a second edge extending away from the proximal end. The fold protection panel has a maximum width that is the greatest distance from the first edge to the second edge and a maximum length that is the distance from the proximal end to the distal end such that after the barrier panel has been folded at or near the barrier panel's midpoint so the barrier panel's second end is brought towards its first end and the side wing on the first edge and the side wing on the third edge are folded over the barrier panel towards or overlapping each other to form at least a partial enclosure. The distal end of the fold protection panel is configured to cover at least the first edge and the third edge of the folded barrier panel.

Referring now to FIGS. 1A through 1E, there is illustrated an example of a multi-panel sterilization assembly in an exemplary sequence of folding prior to sterilization. FIG. 1A illustrates a multi-panel sterilization assembly 100 composed of barrier panel 102 which cooperates with the fold protection panel 108 and the panel attachment means 106 on the first surface 110 so the barrier panel 102 can be folded around the content 200 to form a package (such as the package 202 generally illustrated in FIGS. 1E and 2A). The barrier panel 102 is the portion of the flexible multi-panel sterilization assembly 100 that contacts and covers the content 200.

As generally illustrated in FIG. 1B, the second end 118 of the barrier panel 102 is folded up at the midpoint "M" and the second edge 122 brought towards the first end 114 so part of the barrier panel 102 extends over the content 200. As shown in FIG. 1B, the width of the barrier panel at the second end 118 is less than the width of the barrier panel at the first end 114. This provides a configuration of the fourth edge 126 and the fifth edge 128 that allows access to the panel attachment means 106 after the second end 118 is brought up to the first end 114.

In some embodiments of the present disclosure, a pull tab system 300 and spaced apart pull locations 500 extend from the second end 118 so that the pull tab system 300 is positioned to be accessible during the final steps of unfolding or unwrapping a wrapped package. The pull tab system 300 desirably extends from or is joined to the second end 118 of the barrier panel on the second opposing surface 112 of the barrier panel 102. It is contemplated that the pull tab system 300 may be unitary or integral with the barrier panel. The distal end (i.e., the loose end) of the pull tab system 300 is desirably secured to the barrier panel with a light adhesive or an adhesive tab or sticker such that the pull tab system 300 does not flop around during wrapping and is in an appropriate position during unwrapping.

FIG. 1C illustrates the third edge 124 of the barrier panel 102 is folded over the second end 118 (after the second end 118 is brought up to the first end 114). While not necessarily shown to scale, the third edge 124 of the barrier panel 102 after folding need not extend very far toward the middle of the assembly. FIG. 1C illustrates that the side wing 400a on the third edge 124 is deployed so that the panel attachment means 106 (not visible in FIG. 1C) is used to securely place the third edge against the second end 118 of the barrier panel (i.e., the content covering region).

FIG. 1D shows that the first edge 120 of the barrier panel 102 is folded over the second end 118 (after the second end 118 is brought up to the first end 114). FIG. 1D illustrates that the side wing 400b on the first edge 120 is deployed so that the panel attachment means 106 (not visible in FIG. 1D) is used to securely place the first edge against the second end 118 of the barrier panel (i.e., the content covering region).

As can be seen in FIG. 1D, the panel attachment means 106 are positioned on the side wings 400 so they attach to the second end 118 of the barrier panel (i.e., the content covering region) between the spaced apart pull locations 500 of the pull tab system 300. FIG. 1E illustrates that the first end 114 of the barrier panel 102 is folded over the second end 118. While not necessarily shown to scale, the first end 114 of the barrier panel 102 upon folding need not extend very far toward the middle of the assembly. Accordingly, it is evident that the third edge 124 and the first edge 120 generally do not overlap. Unlike conventional sterilization wrap in which the edges are intentionally overlapped, the edges 120 and 124 of the barrier panel are separated by a distance. This difference highlights the importance of the panel attachment means 106 to hold the folded edges 120 and 124 of the barrier panel 102 in place about the content. Moreover, having these edges generally exposed highlights the importance of the fold protection panel 108.

Referring again to FIGS. 1A, 1D and 1E, the fold protection panel 108 and the portion of the barrier panel 102 between the extremity "E" at the first end 114 of the barrier panel and the pre-determined fold line 116 is folded over bringing the first end 114 of the fold protection panel 108 over the second end 118 of the barrier panel. In some embodiments, a portion of the material adjacent the first edge 120 and the third edge 124 may be visible. With this configuration, the actual edges 120 and 124 of the barrier panel 102 are fully covered so the edges themselves are less susceptible to being accidently pulled open or breached during normal handling of the package. The fold protection panel is typically secured utilizing conventional tape that is used with sterilization wrap. Desirably, the fold protection panel covers the edges of the barrier protection panel after it is folded around the content to be sterilized to form a package. The fold protection panel covers these edges to prevent a worker inadvertently opening the folded barrier protection panel. In addition, the fold protection panel shields the edges from snags, pulls or other phenomenon that could impart a peel force to these edges that would cause the panel attachment means to detach. That is, the configuration of the multi-panel sterilization assembly utilizes the fold protection panel to protect exposed edges of the barrier panel after the barrier panel has been folded around content to be sterilized to form a package.

Figure 2B:
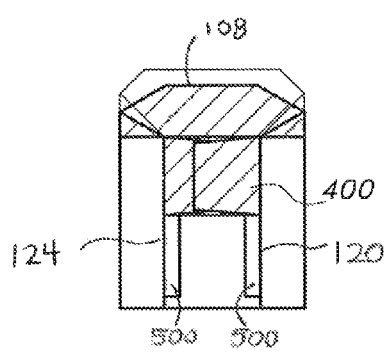
Figure 2C:
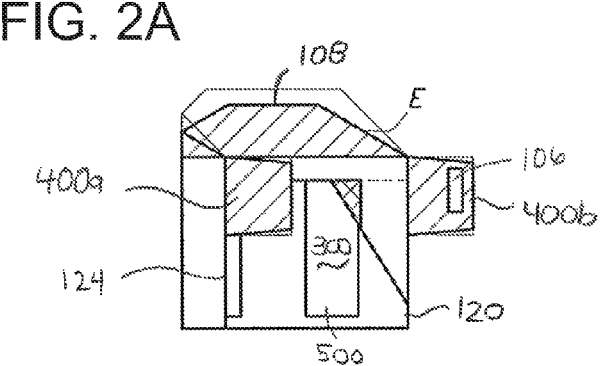
Figure 2D:
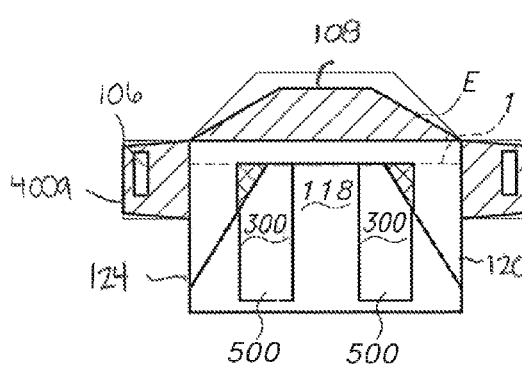

The sequence of unfolding the multi-panel sterilization assembly after it has wrapped around a tray or article and sterilized is generally the reverse of the folding sequence as generally illustrated in FIGS. 2A through 2E. For example, FIG. 2A illustrates a package 202 ready to be unwrapped or unfolded. A conventional tape securing the fold protection panel 108 is broken and the fold protection panel 108 is pulled back to expose the side wings 400 as illustrated in FIG. 2B. The side wings 400 may be pulled up and to the side (away from the center) to detach the panel attachment means such that the first edge 120 and the third edge 124 are unfolded to a configuration as generally illustrated by FIG. 2D. This step may be carried out by pulling the side wings 400 simultaneously or sequentially as shown in FIG. 2C. Importantly, the location/position of the side wings 400, the ability to grip the side wings without compromising sterility, and the leverage and distribution of forces provided by the extended side wings help the fold protection panel, and the first edge 120 and the third edge 124 of the barrier panel remain in a generally flat, unfolded configuration, which keeps them from folding back up over the content 200.

Figure 2E:
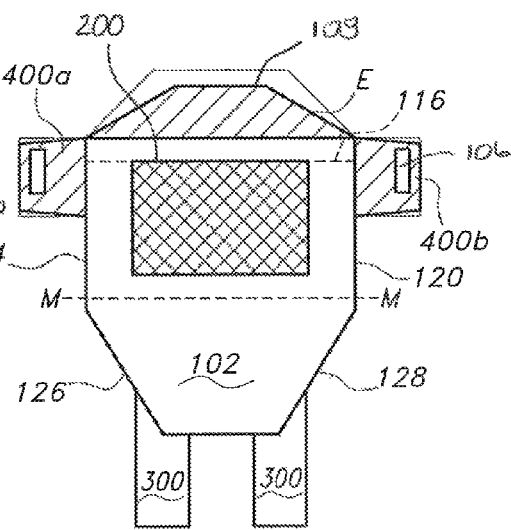

As seen in FIG. 2D, unfolding the side wings 400 exposes the spaced apart pull locations 500 of the pull tab system 300. Each pull location 500 is grasped at a convenient location or at the position when the pull tab system 300 is secured to the barrier panel with an adhesive tab or sticker and the tab or sticker is pulled up. The pull tab system 300 and the second end 118 of the barrier panel is pulled away from the content 200 as shown in FIG. 2E, resulting in complete access to the content 200. Importantly, the spaced apart pull locations 500 help the first edge 120 and the third edge 124 of the barrier panel remain in a generally flat, unfolded configuration which keeps them from folding back up over the content 200.

According to the present disclosure, the barrier panel may be composed of at least one layer of a breathable nonwoven material. Desirably, the breathable nonwoven material is a laminate composed of a layer of spunbonded filaments, a layer of meltblown fibers, and a layer of spunbonded filaments—also called spunbonded-meltblown-spunbonded material. The method of making these layers is known and described in commonly assigned U.S. Pat. No. 4,041,203 to Brock et al which is incorporated herein in its entirety by reference. The material of Brock et al is a three layer laminate of spunbonded-meltblown-spunbonded layers which is also commonly referred to by the acronym "SMS". The two outer layers of SMS are a spunbonded material made from extruded polyolefin fibers, or filaments, laid down in a random pattern and then bonded to one another. The inner layer is a meltblown layer also made from extruded polyolefin fibers generally of a smaller diameter than the fibers in the spunbonded layers. As a result, the meltblown layer provides increased barrier properties due to it fine fiber structure which permits the sterilizing agent to pass through the fabric while preventing passage of bacteria and other contaminants. Conversely, the two outer spunbonded layers provide a greater portion of the strength factor in the overall laminate. The laminate may be prepared using an intermittent bond pattern that is preferably employed with the pattern being substantially regularly repeating over the surface of the laminate. The pattern is selected such that the bonds may occupy about 5-50% of the surface area of the laminate. Desirably, the bonds may occupy about 10-30% of the surface area of the laminate. Other combinations and variations of these materials are contemplated. As a non-limiting example, the inner layer may contain two meltblown layers such that the material may be called "SMMS".

When the barrier panel is composed of or incorporates SMS material(s), the basis weight of the SMS material(s) may be from 1 ounce per square yard or "osy" which is approximately (33 grams per square meter or "gsm") to about 3 osy (100 gsm). For example, the basis weight of the SMS material(s) may be from 1.2 osy (40 gsm) to about 2 osy (67 gsm). As another example, the basis weight of the SMS material(s) may be from 1.4 osy (47 gsm) to about 1.8 osy (60 gsm). The basis weight may be determined in accordance with ASTM D3776-07. Multiple plies or layers of SMS material may be used to provide basis weights ranging from about 2 osy (67 gsm) to about 5 osy (167 gsm).

The permeability of the sheet material of the barrier panel may range from 25 to about 500 cubic feet per minute (CFM) as characterized in terms of Frazier permeability. For example, the permeability of the sheet material barrier panel may range from 50 to about 400 cubic feet per minute. As yet another example, the permeability of the sheet material of the barrier panel may range from 100 to about 300 cubic feet per minute. Alternatively and/or additionally, the permeability of the barrier panel may range from 25 to about 500 cubic feet per minute (CFM) as characterized in terms of Frazier permeability. For example, the permeability of the barrier panel may range from 50 to about 400 cubic feet per minute. As yet another example, the permeability of the barrier panel may range from 100 to about 300 cubic feet per minute. The Frazier permeability, which expresses the permeability of a material in terms of cubic feet per minute of air through a square foot of area of a surface of the material at a pressure drop of 0.5 inch of water (or 125 Pa), was determined utilizing a Frazier Air Permeability Tester available from the Frazier Precision Instrument Company and measured in accordance with Federal Test Method 5450, Standard No. 191A.

When the barrier panel is composed of or incorporates SMS material(s) that have basis weights ranging from about 1 osy (33 gsm) to about 2.6 osy (87 gsm), the permeability of the barrier panel may be lower than 25 cubic feet per minute. For example, when SMS materials having basis weights ranging from about 1 osy (33 gsm) to about 2.6 osy (87 gsm), the permeability of the barrier panel may range from about 20 cubic feet per minute to about 75 cubic feet per minute when determined generally in accordance with ISO 9237:1995 (measured with an automated air permeability machine using a 38 cm$^2$ head at a test pressure of 125 Pa,—exemplary air permeability machine is TEXTEST FX 3300 available from TEXTEST AG, Switzerland). If multiple plies or layers of SMS material are used to provide basis weights ranging from about 2 osy (67 gsm) to about 5 osy (167 gsm), the permeability of the barrier panel may range from about 10 cubic feet per minute to about 30 cubic feet per minute when determined generally in accordance with ISO 9237:1995.

As disclosed herein, one or both of the side wings 400 and/or the fold protection panel 108 may desirably be made from a stretchable material. If only one wing is made from stretchable material it is desired that it be the last wing secured to the wrap. Furthermore, a material may be chosen that shrinks when exposed to sterilizing conditions in order to pull the wrap tighter against the content and to provide a visual cue that the package has been sterilized. Lastly, a material may be chosen to change colors when exposed to sterilizing conditions to provide a visual cue that the package has been sterilized. A material having a combinations of shrinkable and color change characteristics may also be used.

Suitable stretchable materials include conventionally known elastic fibers and materials as well as composite elastic materials. Known elastic materials include those sold under the trade names Lycra®, Spandex®, Nylon®, and the like. It should be noted that while the term "elastic" is used herein, the wing stretchable material need not be elastic in the conventional sense, i.e., it need not recover immediately after being stretched and before being sterilized. It may recover prior to sterilization but should certainly recover by the time sterilization is complete.

Color change upon sterilization may be accomplished by the use of chemical additives that may be incorporated into the fibers from which the stretchable materials are made or inks that may be applied to them by known means such as ink jet printing, melt spraying, and other means. Color change indicators change color, typically from yellow to brown or colorless to black, upon sterilization. Sterilization indicator inks are commercially available from a number of sources, including Shield Sterilization and Packaging Co. Ltd of Anhui, China and Namsa® of Northwood, Ohio and are heavy metal (e.g. lead) free.

As used herein the term "composite elastic material" refers to an elastic material which may be a multicomponent material or a multilayer material in which one layer is elastic. These materials may be, for example, "neck bonded" laminates, "stretch bonded" laminates, "neck-stretch bonded" laminates and "zero strain" laminates.

"Neck bonding" refers to the process wherein an elastic member is bonded to a non-elastic member while only the non-elastic member is extended or necked so as to reduce its dimension in the direction orthogonal to the extension. "Neck bonded laminate" refers to a composite elastic material made according to the neck bonding process, i.e.: the layers are joined together when only the non-elastic layer is in an extended condition. Such laminates usually have cross directional stretch properties. Examples of neck-bonded laminates are such as those described in U.S. Pat. Nos. 5,226,992, 4,981,747, 4,965,122 and 5,336,545 to Morman and U.S. Pat. No. 5,514,470 to Haffner et al.

Conventionally, "stretch bonding" refers to a process wherein an elastic member is bonded to another member while only the elastic member is extended at least about 25 percent of its relaxed length. "Stretch bonded laminate" refers to a composite elastic material made according to the stretch bonding process, i.e.: the layers are joined together when only the elastic layer is in an extended condition so that upon relaxing the layers, the nonelastic layer is gathered. Such laminates usually have machine directional stretch properties and may be stretched to the extent that the nonelastic material gathered between the bond locations allows the elastic material to elongate. One type of stretch bonded laminate is disclosed, for example, by U.S. Pat. No. 4,720,415 to Vander Wielen et al., in which multiple layers of the same polymer produced from multiple banks of extruders are used. Other composite elastic materials are disclosed in U.S. Pat. No. 4,789,699 to Kieffer et al., U.S. Pat. No. 4,781,966 to Taylor and U.S. Pat. Nos. 4,657,802 and 4,652,487 to Morman and U.S. Pat. No. 4,655,760 to Morman et al.

"Neck-stretch bonding" generally refers to a process wherein an elastic member is bonded to another member while the elastic member is extended at least about 25 percent of its relaxed length and the other layer is a necked, non-elastic layer. "Neck-stretch bonded laminate" refers to a composite elastic material made according to the neck-stretch bonding process, i.e.: the layers are joined together when both layers are in an extended condition and then allowed to relax. Such laminates usually have omni-directional stretch properties.

"Zero strain" stretch bonding generally refers to a process wherein at least two layers are bonded to one another while in an untensioned (hence zero strain) condition and wherein one of the layers is stretchable and elastomeric and the second is stretchable but not necessarily elastomeric. Such a laminate is stretched incrementally through the use of one or more pairs of meshing corrugated rolls which reduce the strain rate experienced by the web. "Zero strain stretch laminate" refers to a composite elastic material made according to the zero strain stretch bonding process, i.e.: the elastic and nonelastic layers are joined together when both layers are in an unextended condition and stretched though meshing corrugated rolls. The second layer, upon stretching of the laminate, will be at least to a degree permanently elongated so that the laminate will not return to its original undistorted condition upon release of the stretching force. This results in z-direction bulking of the laminate and subsequent elastic extensibility in the direction of initial stretching at least up to the point of initial stretching. Examples of such laminates and their production processes may be found in U.S. Pat. Nos. 5,143,679, 5,151,092, 5,167, 897, and 5,196,000.

While particular embodiments of the present disclosure have been described herein; it will be apparent to those skilled in the art that alterations and modifications may be made to the described embodiments without departing from the scope of the appended claims.

What is claimed is:

1. A flexible multi-panel sterilization assembly comprising a barrier panel having a first end defining a fold protection panel, an opposing second end, opposing first and third edges, a second edge opposite the first end, and opposing first and second wings to secure portions of the first edge and the third edge to each other or to a portion of the second end after the barrier panel has been folded at or near its midpoint such that its second end is brought towards its first end, wherein at least one of the fold protection panel or wings is made from a stretchable material, further wherein at least one of the protection panel or wings is made from a material that is shrinkable when exposed to sterilizing conditions, wherein the barrier panel includes a first surface configured to cover or contact an item to be sterilized and an opposing second surface.

2. The sterilization assembly of claim 1, wherein the barrier panel has a fourth edge.

3. The sterilization assembly of claim 2, wherein the barrier panel has a fifth edge.

4. The sterilization assembly of claim 1, wherein the first and second wings are located on a second surface of the barrier panel and include grip portions for folding or unfolding the barrier panel.

5. The sterilization assembly of claim 4, wherein the first and second wings comprise adhesive tape, double-sided adhesive tape, cohesive materials, hook and loop fastening systems, mechanical fastening systems, snaps, clips, magnets, catches, slots and tabs, or a combination thereof.

6. The sterilization assembly of claim 1, wherein the sterilization assembly further includes a pull tab system and two spaced apart pull locations.

7. The sterilization assembly of claim 6, wherein the pull tab system is positioned to be accessible during unfolding or unwrapping the item after sterilization.

8. The sterilization assembly of claim 7, wherein the pull tab system extends from or is joined to the second end of the barrier panel.

9. The sterilization assembly of claim 7, wherein the pull tab system extends from or is joined to the second end of the barrier panel at the opposing second surface.

10. The sterilization assembly of claim 6, wherein a distal end of the pull tab system is secured to the second end of the barrier panel with an adhesive or sticker.

11. The sterilization assembly of claim 1, wherein the fold protection panel is formed from a material that is shrinkable when exposed to sterilizing conditions.

12. The sterilization assembly of claim 1, wherein the first and second wings are made from a material that is shrinkable when exposed to sterilizing conditions.

13. The sterilization assembly of claim 1, wherein the fold protection panel is made from a material that changes color when exposed to sterilizing conditions.

14. The sterilization assembly of claim 1, wherein the first and second wings are made from a material that changes color when exposed to sterilizing conditions.

15. The sterilization assembly of claim 1, wherein the fold protection panel is made from a material that changes color when exposed to sterilizing conditions.

16. The sterilization assembly of claim 1, wherein the barrier panel has a Frazier permeability of from about 25 cubic feet per minute to about 500 cubic feet per minute.

17. The sterilization assembly of claim 3, wherein the barrier panel is configured such that a width of the second end of the barrier panel is less than a width of the first end of the barrier panel, resulting in a configuration of the fourth edge and the fifth edge that allows access to panel attachment means located on the first and second wings after the second end is brought towards the first end.

18. The sterilization assembly of claim 17, wherein the panel attachment means are configured to be secured to the opposing second surface of the barrier panel at the second end.

* * * * *